(12) United States Patent
Sano et al.

(10) Patent No.: US 7,998,120 B2
(45) Date of Patent: Aug. 16, 2011

(54) PREFILLED SYRINGE AND PRODUCTION METHOD FOR A BARREL THEREOF

(75) Inventors: Minoru Sano, Osaka (JP); Yoshihisa Hama, Osaka (JP)

(73) Assignee: Nipro Corporation, Osaka (JP)

( * ) Notice: Subject to any disclaimer, the term of this patent is extended or adjusted under 35 U.S.C. 154(b) by 1420 days.

(21) Appl. No.: 10/762,530

(22) Filed: Jan. 23, 2004

(65) Prior Publication Data

US 2004/0267194 A1  Dec. 30, 2004

(30) Foreign Application Priority Data

Jan. 28, 2003  (JP) .................................. 2003-019401

(51) Int. Cl.
*A61M 5/00*  (2006.01)
*A61M 5/31*  (2006.01)

(52) U.S. Cl. ....................................... 604/187; 604/241

(58) Field of Classification Search ............... 604/93.01, 604/187, 410, 103.06, 232, 110, 240, 241
See application file for complete search history.

(56) References Cited

U.S. PATENT DOCUMENTS

| | | | | |
|---|---|---|---|---|
| 3,375,825 | A | * | 4/1968 | Keller ............................ 604/193 |
| 4,535,901 | A | | 8/1985 | Okudaira et al. ................ 215/1 C |
| 5,125,898 | A | * | 6/1992 | Kaufhold et al. ................ 604/110 |
| 5,131,830 | A | | 7/1992 | Orimoto et al. ................. 425/130 |
| 5,554,125 | A | * | 9/1996 | Reynolds ........................ 604/187 |
| 5,871,477 | A | * | 2/1999 | Isono et al. ..................... 604/410 |
| 5,899,889 | A | * | 5/1999 | Futagawa et al. ............... 604/232 |
| 6,053,895 | A | * | 4/2000 | Kolberg et al. ................. 604/218 |
| 6,331,174 | B1 | * | 12/2001 | Reinhard et al. ............... 604/232 |
| 6,544,233 | B1 | * | 4/2003 | Fukui et al. .................... 604/191 |
| 2003/0032928 | A1 | * | 2/2003 | Sudo et al. ..................... 604/225 |
| 2005/0119620 | A1 | | 6/2005 | Tachikawa et al. ........... 604/187 |

FOREIGN PATENT DOCUMENTS

| | | |
|---|---|---|
| JP | 10-57446 A | 3/1998 |
| JP | 11-332984 A | 12/1999 |
| WO | 02/102571 A1 | 12/2002 |
| WO | WO 02102571 | * 12/2002 |

OTHER PUBLICATIONS

Weller, Thomas; Shulz, Detlef B.; McNally, Donal (1997). New engineering polyolefin offers clear processing opportunities. Plastics Technology.*

Shin, Ju Young; Park, Ji Young; Liu, Chenyang; He, Jiasong; and Kim, Sung Chul. Chemical structure and physical properties of cyclic olefin copolymers (IUPAC Technical Report). (2005). Pure and Applied Chemistry. vol. 77, No. 5, pp. 801-814.*

* cited by examiner

*Primary Examiner* — Nicholas D Lucchesi
*Assistant Examiner* — Nathan R Price
(74) *Attorney, Agent, or Firm* — Kubovcik & Kubovcik (57) ABSTRACT

A prefilled syringe composed of a barrel having a luer tip at one end and an open proximal end, the barrel having at least a three layer structure of an innermost layer, an outermost layer, both made of a polyolefin resin, and an intermediate layer made of a resin with a barrier property and sandwiched by the innermost layer and the outermost layer. The barrel is produced through the sequential steps of: (a) injecting a specific amount of a polyolefin resin inside a cavity; (b) injecting a specific amount of a resin excelling in barrier property; (c) injecting a specific amount of the polyolefin resin again; and (d) separating the luer tip surface and an injection unit by pushing off a valve pin provided inside a valve gate or an inner nozzle of the injection unit, which injects the resin excelling in barrier property, toward the direction of the luer tip surface as desired.

2 Claims, 9 Drawing Sheets

PREFILLED SYRINGE AND PRODUCTION METHOD FOR A BARREL THEREOF

BACKGROUND OF THE INVENTION

1. Field of the Invention

The present invention relates to a prefilled syringe and to a production method for a barrel thereof and, more specifically, to a prefilled syringe excelling in gas barrier property and water vapor barrier property and to a production method for a barrel thereof.

2. Description of the Related Art

A prefilled syringe containing, in advance, a medication inside a barrel is prevailing recently for reasons such as savings of time of transferring the medication from a container to the syringe and a low risk of contamination by bacteria. A prefilled syringe with a non-breakable plastic barrel is generally used.

However, a prefilled syringe with a plastic barrel has problems such as deterioration of the medication caused by oxygen and evaporation of water from the medication. If the barrel is molded by a resin with barrier properties to avoid these problems, a problem such as elution occurs, involving another problem concerning safety. Therefore, a prefilled syringe with a plastic barrel is generally packaged along with a deoxidant or the like using an external packaging material made of a film which excels in gas barrier property or water vapor barrier property. The packaging step complicates production, and the packaging material makes storage cumbersome, taking significant space as a whole. Further, the packaging material and the deoxidant must be disposed of as waste after use, and it is hardly ecologically friendly. Further, in the case where only a heat-labile resin such as polyethylene can be used in order to prevent an interaction with the medication, the barrel itself may be deformed by high pressure steam sterilization.

Although a glass barrel does not have such faults as described above, it is brittle and variations occur in dimensional accuracy; hence it is not yet widely used.

There is also an invention of coating the whole outer wall surface of a barrel with a film having a gas barrier property. The film is made of materials, such as polyvinylidene chloride (PVDC), having a water vapor permeability of 20 g/m$^2$·24 h (at 40° C., 90% RH) and may be deposited with aluminum. This prevents penetration of water vapor, oxygen, or the like through a wall surface into the barrel. Thus, the need for packaging the whole prefilled syringe along with a deoxidant or the like can be eliminated, thereby achieving a reduction in production steps as well as in storage space (see Japanese laid-open publication No. JP 11-332984 A).

Further, as an invention imparting a gas barrier property to a barrel itself, other than the invention of the above JP 11-332984 A, there is an invention in which 90% or more of an amorphous silicon oxide ($SiO_m$) layer, which is obtained by baking a polysilazane film in an oxidizing atmosphere, is formed on a wall surface of the barrel at a thickness of 0.05 to 20 μm (see Japanese laid-open publication No. JP 10-57446 A).

In addition, there is an invention of obtaining a multilayer parison by sequentially and alternately injecting two or more kinds of molten thermoplastic resins into one mold with shifting injection timing from a molding machine having plural injection cylinders with one mold closing operation. Herewith, the multilayer parison, which is a preform for a hollow container, is sanitary and excels in gas permeability resistance and water permeability resistance. The multilayer parison can be obtained using a polyethylene terephthalate (PET) resin or a polyamide resin containing a meta-xylylene group as an intermediate layer and using the PET resin for inner and outer surface layers. A hollow container also usable for medical applications may be obtained by blow molding the multilayer parison (see U.S. Pat. No. 4,535,901).

However, although JP 11-332984 A does not mention a method of coating an outer wall of a syringe barrel with a film having a gas barrier property, an adhesive or a bonding layer is required for bonding the film on the barrel. In addition, it is difficult to coat the whole cylindrical barrel. When shrink packaging, the gas barrier property may not be ensured because the film and the syringe do not completely bond. Further, ethylene vinyl alcohol copolymer (EVOH), which is a typical gas barrier material, significantly degrades in barrier property by high pressure steam sterilization, so even if the outer wall of the barrel could be supposedly coated, it is pondered whether a desirable effect will be obtained.

On the other hand, when producing a barrel for a prefilled syringe using the method described in JP 10-57446 A, the method must go through 5 stages of the steps of (a) molding the barrel with a predetermined resin, (b) applying a polysilazane solution to the barrel, (c) removing an organic solvent in the polysilazane solution by drying in an oxygen atmosphere at 60° C. or less, (d) forming an amorphous silicon oxide layer by baking the barrel at a temperature of 60° C. to 200° C., and (e) forming a protective film with an epoxy resin or the like on the outermost layer. The production method is thus complicated, and it cannot be said that production efficiency is satisfactory. Further, polysilazane hydrolyzes when coming in contact with water and an alcohol solvent; therefore, an aromatic hydrocarbon such as xylene or petroleum ether must be inevitably used for a solvent. It takes time to completely remove those organic solvents, and in a case of incomplete removal thereof, a problem arises in terms of safety of the medication. Further, polysilazane produces pyrophoric silane gas, so control and handling thereof are difficult.

Further, the method described in U.S. Pat. No. 4,535,901 relates to a production method for a parison, which is a preform for a hollow container to be obtained by blow molding, and is not related to a barrel of a medical syringe with both ends opened and a production method thereof.

BRIEF SUMMARY OF THE INVENTION

The inventors of the present invention, devoting themselves to research for solving the problems described above, have completed the present invention.

That is, the present invention relates to:

(1) a prefilled syringe including: a shoulder portion provided with a luer tip for connecting an injection needle at the tip; a barrel with an opened proximal end; and a gasket inserted from the proximal end of the barrel in a fluid-tight manner while being freely slidable, a medication being contained inside the barrel, in which the barrel has a multilayer structure in which an innermost layer and an outermost layer are both made of a polyolefin resin, and an intermediate layer is composed of at least one layer made of a resin excelling in barrier property.

(2) a prefilled syringe according to the above-mentioned (1), in which the intermediate layer is formed up to the vicinity of a luer tip surface.

(3) a prefilled syringe according to the above-mentioned (1), in which a tip of the intermediate layer in a cylindrical wall portion of the barrel is formed up to a rim of the shoulder portion, the shoulder portion is formed with the polyolefin resin to a thickness which exerts a barrier property, and the luer tip is sealed by a cap having a barrier property.

(4) a prefilled syringe according to any one of the above-mentioned (1) to (3), in which the intermediate layer is formed toward a direction of the proximal end of the barrel from a proximal end of a presumed insertion position of the gasket inserted in the barrel.

(5) a production method for a barrel according to any one of the above-mentioned (1) to (4) including the steps of: (a) injecting a specific amount of a polyolefin resin from a gate of a cavity provided at a position corresponding to a luer tip surface of the barrel; (b) sequentially injecting a specific amount of a resin excelling in a barrier property; (c) injecting a specific amount of the polyolefin resin again; and (d) separating the luer tip surface and an injection unit by pushing off at least one of a valve pin provided inside a valve gate and an inner nozzle of the injection unit, which injects the resin excelling in a barrier property toward the luer tip surface.

(6) a production method for a barrel according to any of one of the above-mentioned (1) to (4) including the steps of: (a) injecting a specific amount of a polyolefin resin inside a cavity from a gate provided at an arbitrary position of the shoulder portion of the barrel; and (b) sequentially injecting a specific amount of a resin excelling in a barrier property.

It should be note that "barrier property" refers to a "gas barrier property", "water vapor barrier property", or "gas barrier property and water vapor barrier property". "Excelling in gas barrier property" means that an oxygen permeability at 25° C., 50% RH, is 2 ml/m$^2$·24 hr·atm/25 μm or less. "Excelling in water vapor barrier property" means that a water vapor permeability at 40° C., 90% RH, is 10 g/m$^2$·24 hr·atm/25 μm or less. Further, "having barrier property" refers to having a feature excelling in a barrier property described above.

Further, "excelling in thermal resistance" refers to enduring high pressure steam sterilization under harsh conditions such as at 105° C. for 30 minutes or more. "Elution" refers to an elution of a resin component into a medication or an elution of a plasticizer contained in the resin component.

BRIEF DESCRIPTION OF THE DRAWINGS

FIG. 1(a)-(c) is a diagram showing an embodiment of the present invention. Part (a) is a longitudinal sectional view, and part (b) is a cross sectional view taken along line A-A (the gasket is not shown).

DETAILED DESCRIPTION OF THE INVENTION

Figure 1A:
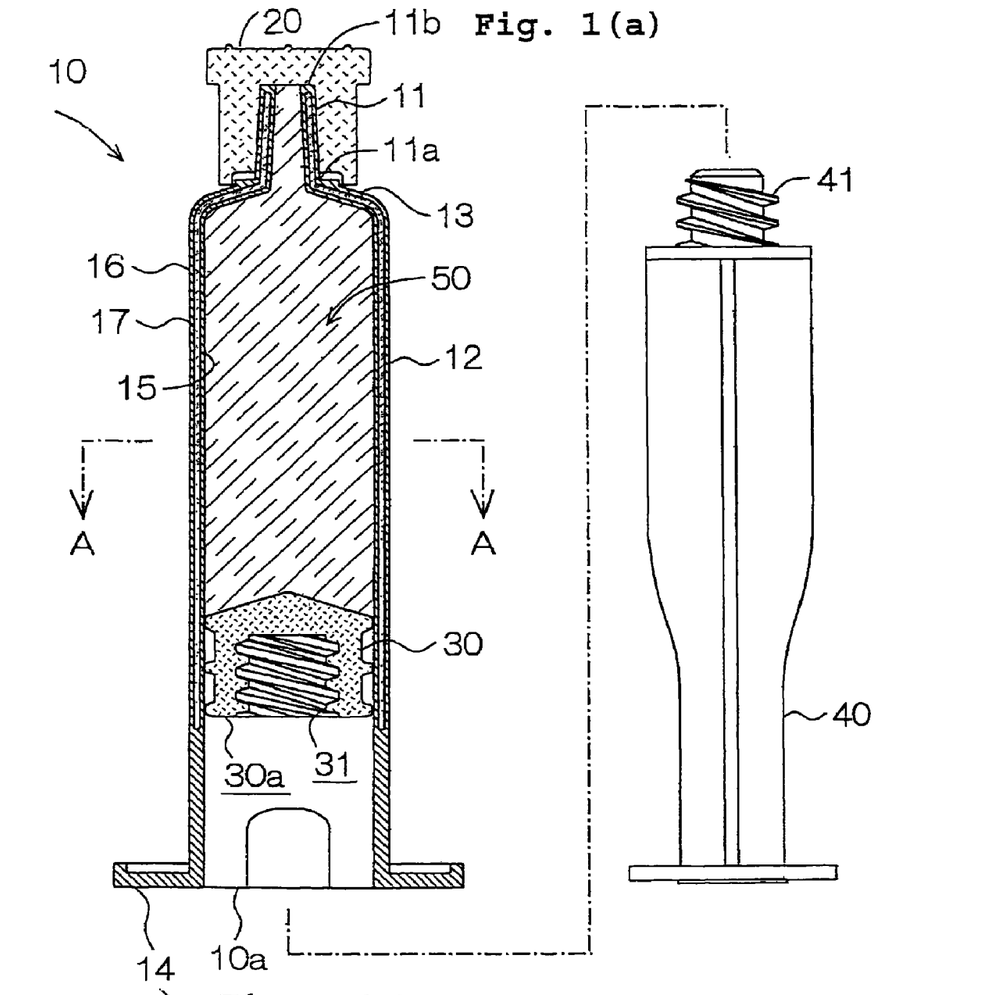
Figure 2:
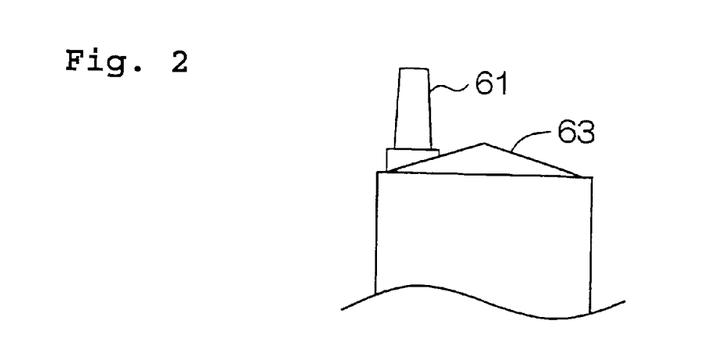
FIG. 2 is a partial view showing another embodiment of the present invention, in which a syringe is a so-called eccentric luer tip type syringe and has a luer tip provided in a position eccentric from the center.

First, a barrel for a prefilled syringe of the present invention is described. As shown in FIG. 1(a), a preferably adopted shape of the barrel 10 of a prefilled syringe of the present invention is a cylindrical shape having a male "Luer-taper" luer tip 11 at the tip, where an injection needle can be connected in a fluid-tight manner, a shoulder portion 13 formed from a proximal end 11a of the luer tip 11 to a cylindrical wall 12, and a finger-hooking flange 14 at an opened proximal end 10a. The luer tip 11 is sealed in a fluid-tight manner by a cap 20. Further, a gasket 30 is inserted in the barrel 10 in a fluid-tight manner while being freely slidable. The gasket 30 can be connected with a plunger 40 at a proximal end 30a. The space from the gasket 30, inserted inside the barrel 10, to the luer tip 11 can contain a medication 50. A position for providing the luer tip 11 does not have to be at the center of the shoulder portion 13. As shown in FIG. 2, a luer tip 61 may be provided in a position eccentric from the center of a shoulder portion 63.

Figure 1B:
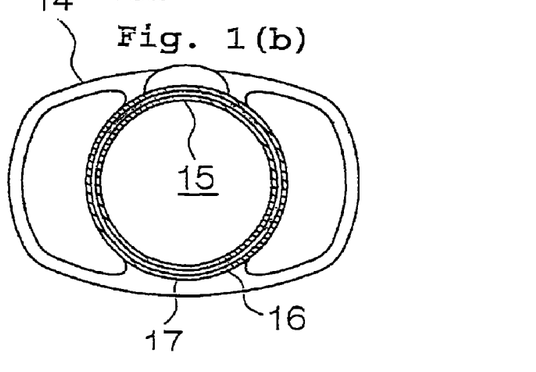

As shown in FIGS. 1(a) and (b), the barrel 10 has at least a three-layer structure of an innermost layer 15, an outermost layer 16, and an intermediate layer 17 between the innermost layer 15 and the outermost layer 16. The innermost layer 15 and the outermost layer 16 are preferably formed from the same material, and examples of preferable materials include polyethylene, polypropylene, a mixture of polyethylene and polypropylene, and a polyolefin resin such as cyclic polyolefin. However, any resin known for use as a medical material such as polycarbonate, a methacrylate resin, and poly (4-methyl-1-pentene), which does not interact with the medication 50 contained inside the barrel 10, and having no risk of elution or the like can be preferably adopted. Further, the material for the intermediate layer 17 is selected from a resin excelling in a gas barrier property, a resin excelling in a water vapor barrier property, and a resin excelling in thermal resistance. Examples of resins excelling in a gas barrier property and a water vapor barrier property include an ethylene vinyl alcohol copolymer, polyacrylonitrile, vinylidene chloride, polyvinyl alcohol, nylon, polyester, or the like. Examples of a resin excelling in thermal resistance include polypropylene, poly-4-methylpentene-1, polyester, polycarbonate, polyether imide, polyacrylate, or the like. The intermediate layer 17 is not required to be a single layer and may be a multilayer structure with two or more layers.

As described, by sandwiching a resin excelling in barrier property or thermal resistance with a resin having a low risk of interacting with a medication or eluting thereinto, a barrel for a prefilled syringe, which has a low risk of interacting with a medication or eluting thereinto, excels in barrier property, and is highly safe, can be provided.

When only resins having low thermal resistance are adopted for the innermost layer and the outermost layer because of limitations concerning interaction with a medication, deformation of the barrel can be avoided even when conducting a high pressure steam sterilization such as at 105° C. for 30 minutes, at 121° C. for 20 minutes, or the like by forming an intermediate layer using a thermal resistant resin.

Figure 3:
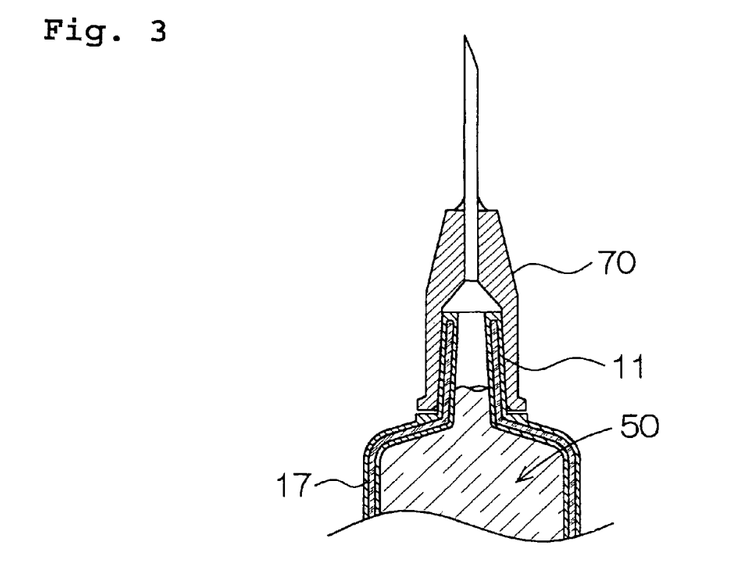
FIG. 3 is a partial longitudinal sectional view showing a state during use of a syringe of an embodiment of the present invention and shows a state of an injection needle connected to a luer tip.

As shown in FIG. 1(a), securing of the barrier property of the barrel 10 is further ensured by forming the intermediate layer 17 up to the vicinity of the luer tip surface 11b. However, the intermediate layer 17 must not be exposed at the luer tip surface 11b. The reason is that if a gap exists between the luer tip surface 11b and a cap 20, the medication 50 and the luer tip surface 11b are at a high risk of coming into contact with each other. Also as shown in FIG. 3, in a case of connecting an injection needle 70 to the luer tip 11 during use, the medication 50 and the luer tip surface 11b have a high chance of coming into contact with each other, so there is a risk of elution from the intermediate layer 17 into the medication 50.

Figure 4:
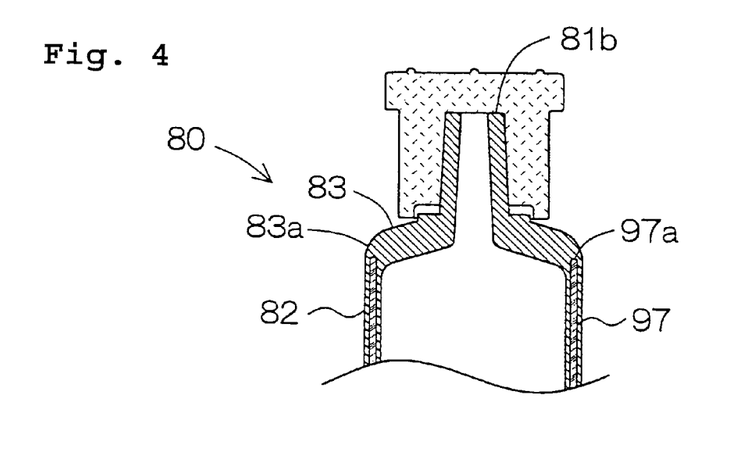
FIG. 4 is a diagram showing another embodiment of the present invention in which an intermediate layer is formed up to a thickly formed shoulder portion rim.

Further as shown in FIG. 4, a tip 97a of an intermediate layer 97 of a cylindrical wall portion 82 of a barrel 80 can be formed up to a rim portion 83a of a shoulder portion 83. However, in this case, the shoulder portion 83 must be provided with a barrier property by molding a thick portion of the polyolefin resin. The cylindrical wall portion 82 of the barrel 80, for visually observing a time course of medication contained therein and insoluble contaminants, must be provided with high transparency and, thus, cannot be thickly molded. Therefore, providing a barrier property by the intermediate layer 97 is indispensable.

Further as shown in FIG. 1(a), the intermediate layer 17 does not have to be formed in the direction of the proximal end 10a from the proximal end 30a of an expected (initial) insertion position of the gasket 30 to be inserted inside the barrel 10. In the space from the proximal end 30a of the gasket 30 to the proximal end 10a of the barrel 10, a medication does not exist. Therefore, there is no need to provide a barrier property.

The gasket 30 is formed of a butyl rubber, a thermoplastic elastomer, or the like. The proximal end thereof is provided with a securing means such as a female screw 31 with which the plunger 40 provided with a male screw 41 at the tip thereof can be secured.

The cap 20 is formed of a butyl rubber, a thermoplastic elastomer, or the like. As shown in FIG. 4, when the intermediate layer is not formed up to the vicinity of a luer tip surface 81b, the cap must have a thickness which ensures a sufficient gas barrier property and water vapor barrier property.

The medication 50 may be any of a solid preparation and a liquid solution. However, a solution that causes problems of an increase in concentration and a decrease in volume by water vapor evaporation is preferable. Among them, a solution, the quality of which degrades from the effect of oxygen, is most preferable.

Figure 5:
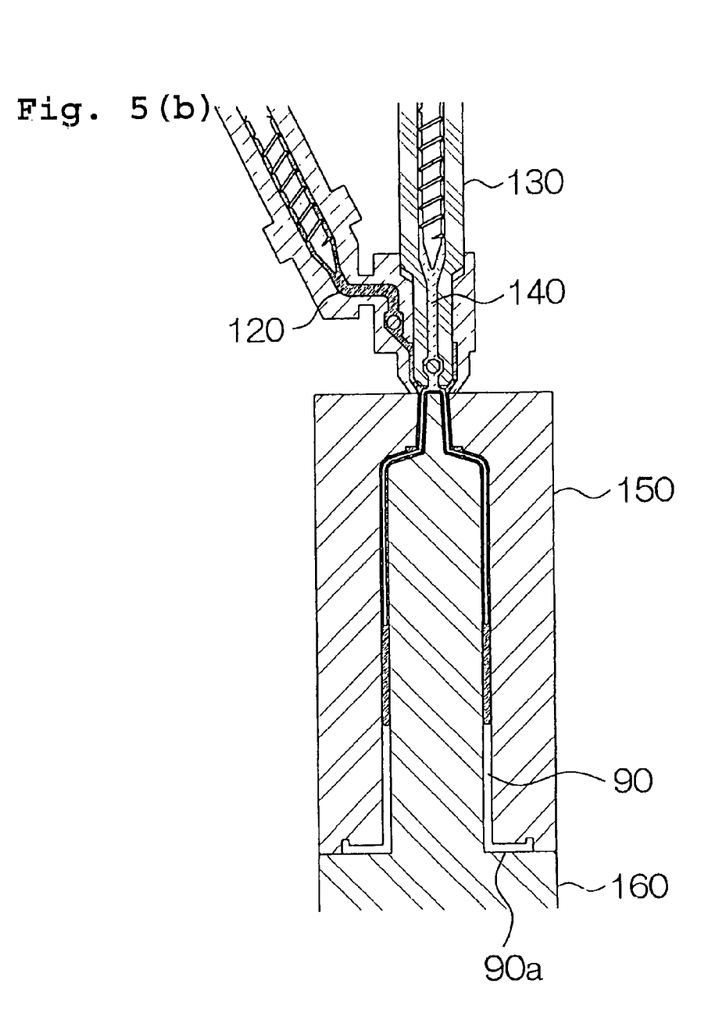
FIG. 5(a)-(c) is a diagram showing steps of a production method of a barrel according to the present invention. The production method includes injecting resins from a gate provided at a luer tip surface.

Next, a production method for a barrel used for a prefilled syringe according to the present invention is described. As shown in FIG. 5(a), first, a polyolefin resin 120 is injected from a gate 100, provided at a position corresponding to the luer tip surface of the barrel portion of a cavity 90, into the cavity 90 using a first injection unit 110.

Then, as shown in FIG. 5(b), after injecting a specific amount of the polyolefin resin 120, a resin excelling in a barrier property 140 is injected into the cavity 90 using a second injection unit 130. The polyolefin resin 120 which is injected first is cooled on wall surfaces of cavity mold 150 and core mold 160 to form a skin layer. The resin excelling in barrier property 140 becomes a core layer having fluidity, moving through a gap of the skin layer toward an end portion 90a of the cavity 90. The amount of the polyolefin resin 120 injected first is preferably adjusted so that the proximal end 10a of the barrel 10 to the proximal end 30a of the gasket 30 is eventually filled, as shown in FIG. 1(a). The reason is that the intermediate layer 17 does not necessarily have to be formed in the direction of the proximal end 10a of the barrel 10 from the proximal end 30a of the gasket 30.

Figure 5C:
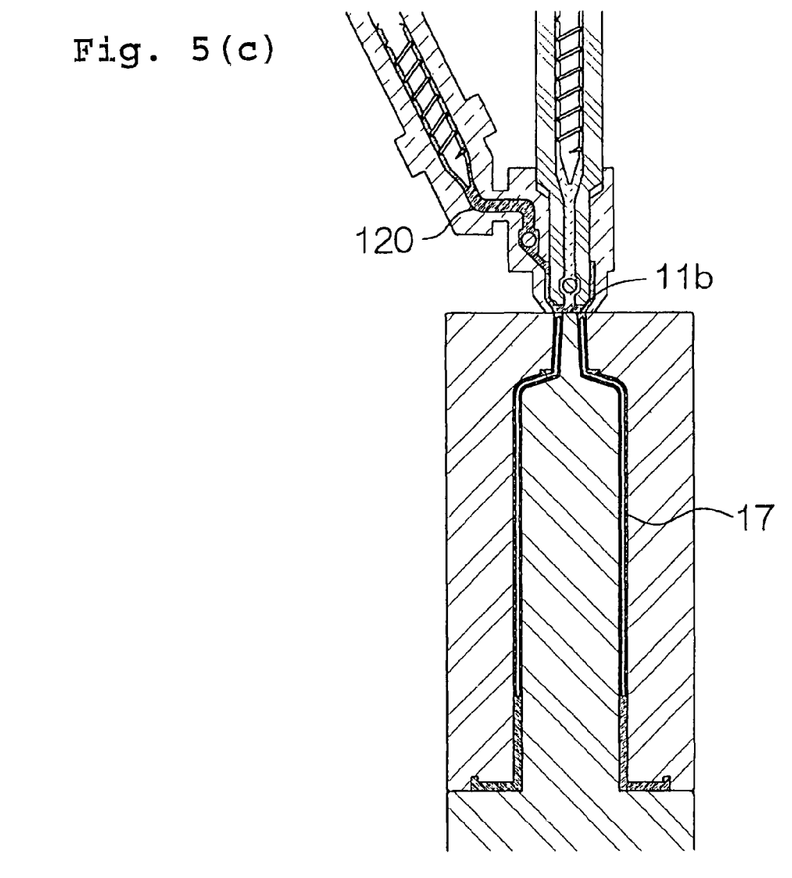
Figure 6A:
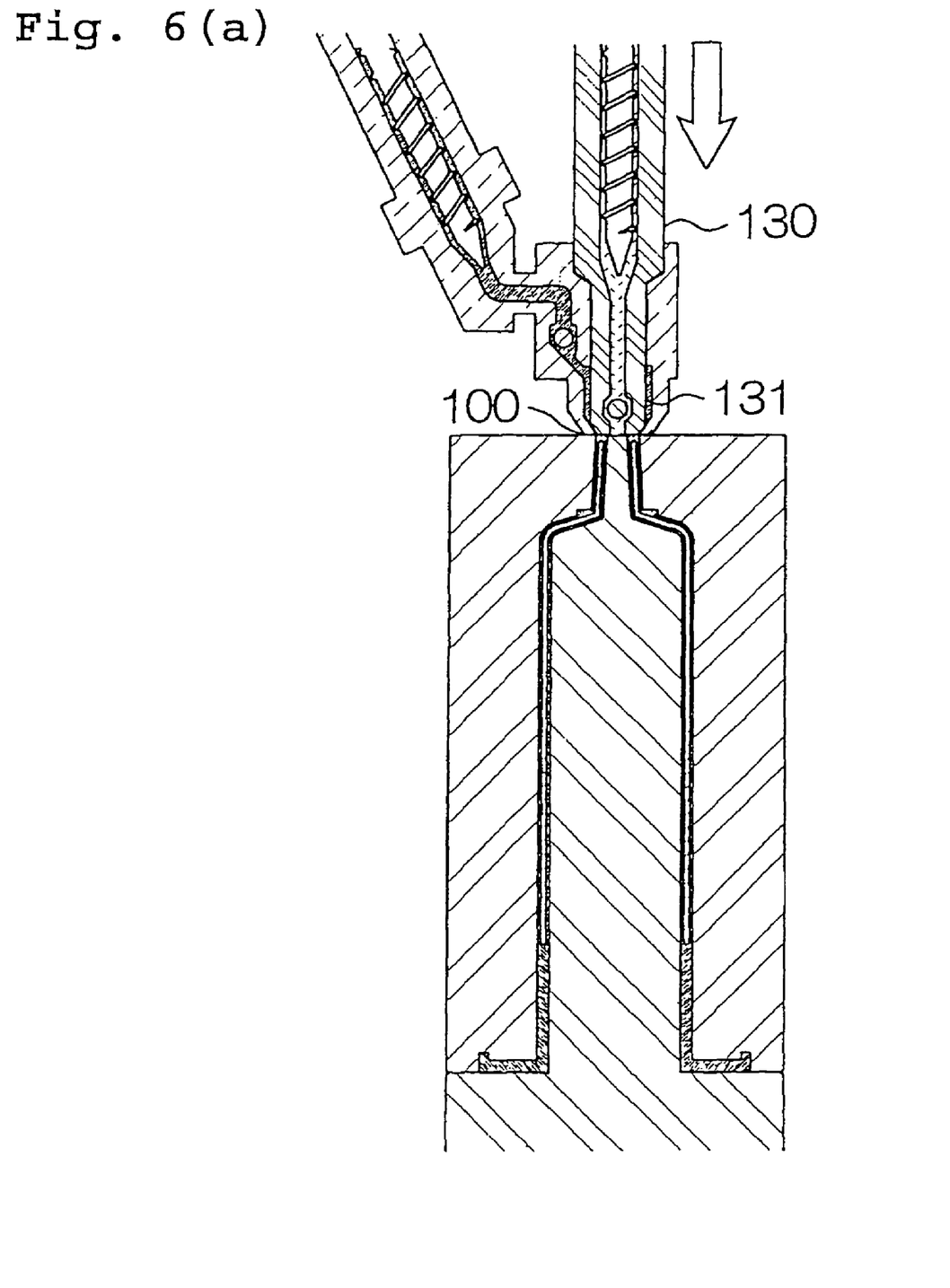
FIG. 6(a)-(b) is a diagram showing steps of a production method of a barrel according to the present invention. The production method separating a product and an injection unit by pushing off of an inner nozzle.
Figure 6B:
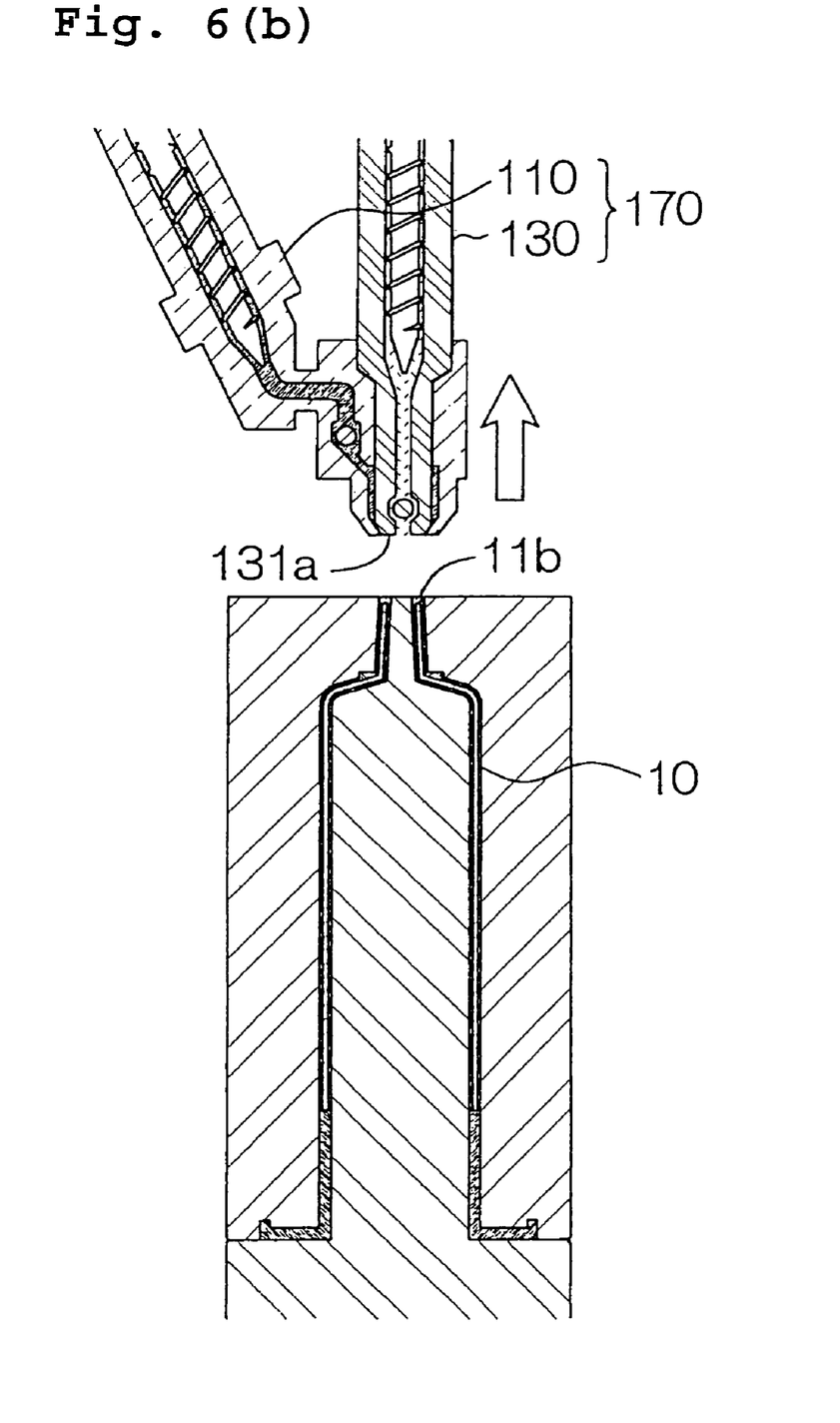

After injecting a specific amount of the resin excelling in barrier property 120, the polyolefin resin 120 is injected again as shown in FIG. 5(c). By pushing off an inner nozzle 131 of the second injection unit 130 toward the direction of the gate 100 as shown in FIG. 6(a), the injection unit 170 and the luer tip surface 11b are separated as shown in FIG. 6(b), thereby producing a barrel for a prefilled syringe used in the present invention. The polyolefin resin injection of a specific amount in advance may be stopped after injecting the specific amount, or the injection of the resin excelling in barrier property may be started without stopping the injection as described, for example, in U.S. Pat. No. 4,535,901 which is incorporated herein by reference.

Figure 7:
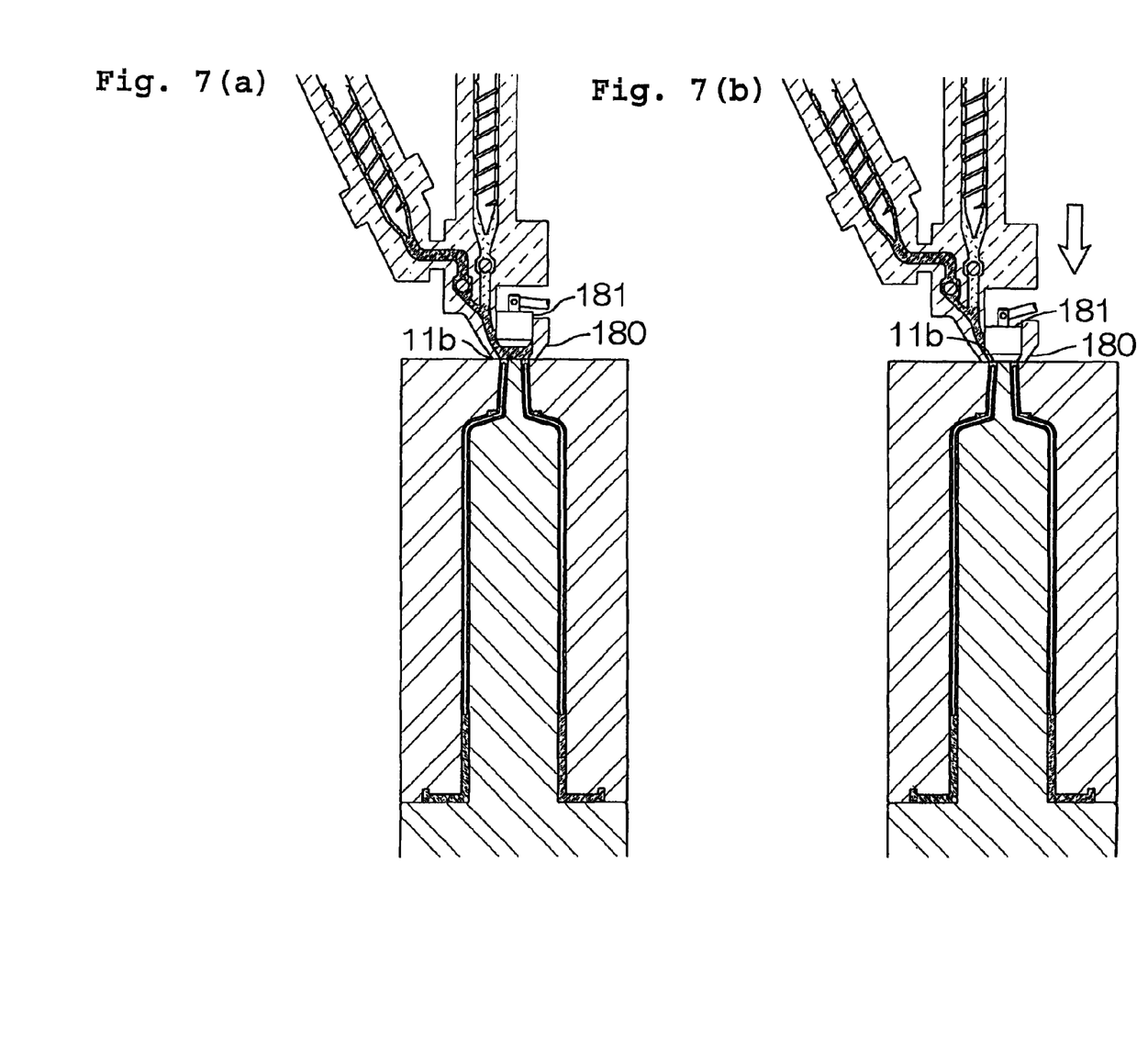
FIG. 7(a)-(b) is a diagram showing steps of another production method of a barrel according to the present invention. The production method includes separating a product and an injection unit by pushing off of a valve pin inside a valve gate.

A tip 131a of the inner nozzle 131 is preferably pushed off to come closely into contact with the luer tip surface 11b. The reason is that by doing so, an unnecessary runner does not remain in the luer tip surface 11b, so that adjustment of dimensional accuracy of the luer tip surface 11b is not required after injection molding. Further, as shown in FIG. 7, a valve pin 181 provided inside a valve gate 180 may be pushed off toward the direction of the luer tip surface 11b instead of pushing off the inner nozzle 131. The pushing off step of the inner nozzle 131 or the valve pin 181 is preferably conducted after the luer tip surface 11b is coated with the polyolefin resin 120 as shown in FIG. 5(c). The reason is that, as described before, the intermediate layer 17 composed of a resin excelling in barrier property 140 must not be exposed at the luer tip surface 11b.

When pushing off of the inner nozzle 131 or the valve pin 181 is not conducted, a runner is formed at the luer tip surface 11b. The runner may be cut off after taking the barrel out from the mold.

Next, another production method of a barrel for a prefilled syringe of the present invention is described.

Figure 8:
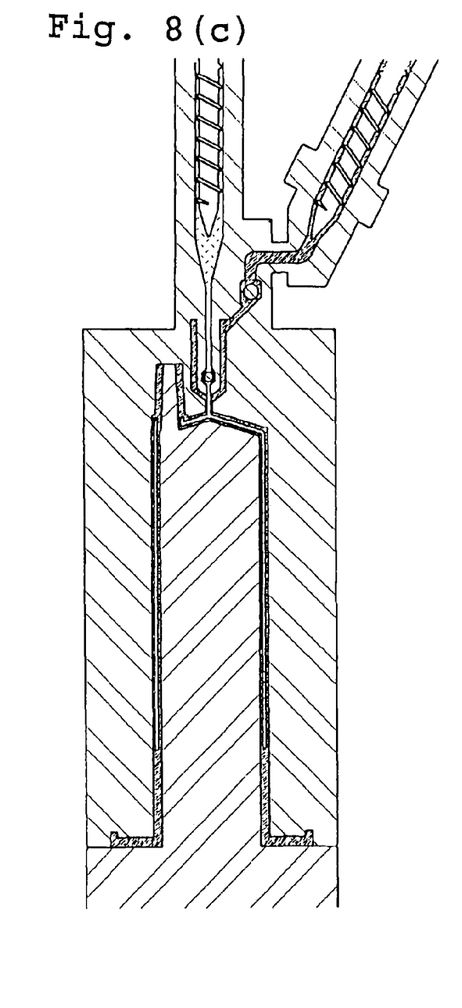
FIG. 8 is a diagram showing another production method of a barrel according to the present invention.
Figure 8A:
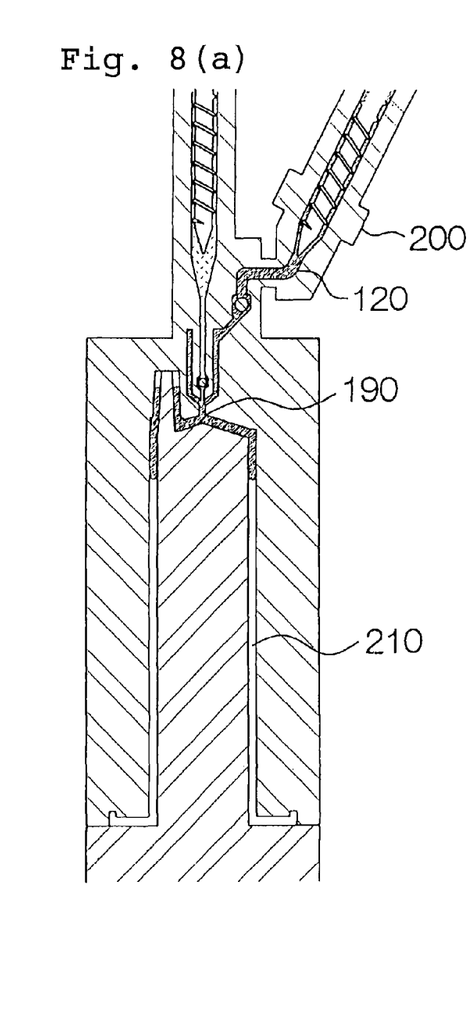

As shown in FIG. 8(a), the polyolefin resin 120 is first injected from a gate 190, provided at a position corresponding to the center of the luer tip surface of the barrel, into a cavity 210 using a first injection unit 200.

Figure 8B:
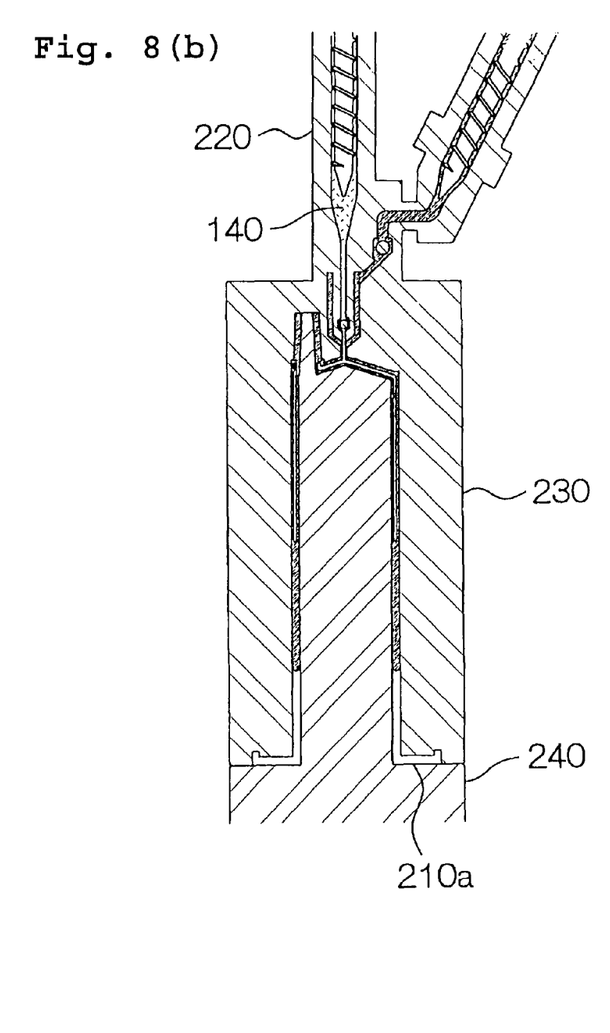

Then, as shown in FIG. 8(b), after injecting a specific amount of the polyolefin resin 120, the resin excelling in barrier property 140 is injected into the cavity 210 using a second injection unit 220. The polyolefin resin 120 which is injected first is cooled at the wall surfaces of cavity mold 230 and core mold 240 to form a skin layer. The resin excelling in barrier property 140 becomes a core layer having fluidity and moves through the space toward the direction of an end 210a of the cavity 210 to eventually reach the state shown in FIG. 8(c). The resin excelling in barrier property 140 does not have to fill the portion inside the luer tip 61. The reason is that the luer tip 61 is sealed with the cap 20 or the like, so the cap 20 or the like provides a barrier property to the luer tip portion 61. The amount of the polyolefin injected first is preferably adjusted so that the proximal end 10a of the barrel to the distal end 30a which is the expected insertion position of the gasket 30 is filled as described with reference to FIG. 1.

After injecting a specific amount of the resin excelling in barrier property 140, the injection of the resin 140 is stopped. After taking out the molded product from the mold, an unnecessary runner is removed, thereby producing the prefilled syringe barrel of the present invention. The injection of the polyolefin resin in a specific amount in advance may be stopped after injecting the specific amount, or the injection of the resin excelling in barrier property may be started without stopping the injection. Further, if it is not desired to leave an unnecessary runner at the gate, a method using the inner nozzle or the valve gate and the valve pin, as shown in FIG. 6 or FIG. 7, can be used.

The gate can be provided at an arbitrary position of the barrel tip surface. However, when providing the gate in a position eccentric from the center of the tip surface, a weld line appears on the cylindrical wall of the barrel located symmetric to the central axis of the gate and the barrel. This creates a risk that the intermediate layer is not formed because the second resin does not pervade through the weld line. Therefore, it is preferable to provide the gate at the center of the tip surface of the barrel by decentering the position of the luer tip when not providing a gate at the luer tip surface.

Further, to produce a multilayer structure having two or more layers of an intermediate layer of the barrel for a prefilled syringe of the present invention, the number of injection units may be increased to inject the successive resin after stopping the injection of the prior resin as the first resin, second resin, third resin, and so on. Alternatively, timing of the start of the injection inside the cavity may be sequentially adjusted.

As described above, according to the present invention, a gas barrier property and a water vapor barrier property can be imparted to a barrel for a prefilled syringe solely through a step of injecting a resin into a single mold. In other words, a gas barrier property, a water vapor barrier property, and a thermal resistance property can be easily imparted with about the same effort and time as a general production method for a syringe. In addition, an adhesive or a bonding layer does not have to be provided, and a portion in contact with a medication is totally coated with the polyolefin resin. Therefore, a risk of interaction of the medication with the barrel or elution of resin used for the barrel during sterilization or storage is low, and safety is extremely high. Further, a container itself has a barrier property, so external packaging material becomes unnecessary, contributing to a savings in resources as well as a savings in storage space, and thereby being convenient for carrying.

What is claimed is:

1. A prefilled syringe comprising: a shoulder portion provided with a luer tip arranged to be connected to an injection needle at a tip thereof; a barrel closed by the shoulder portion and having an open proximal end; and a gasket inserted adjacent to the open proximal end of the barrel in a fluid-tight manner while being freely slidable, a medication being contained inside the barrel, wherein the barrel has a multilayer structure in which an innermost layer and an outermost layer are both made of a polyolefin resin, and an intermediate layer is sandwiched by the innermost layer and the outermost layer and the intermediate layer is composed of at least one layer made of a resin excelling in an oxygen and/or water vapor barrier property, and further wherein the intermediate layer is formed up to a vicinity of a surface of the tip of the luer tip, and is not formed in a direction of the proximal end of the barrel from a proximal end of an initial insertion position of the gasket inserted in the barrel.

2. A prefilled syringe comprising: a shoulder portion provided with a luer tip arranged to be connected to an injection needle at a tip thereof; a barrel closed by the shoulder portion and having an open proximal end; and a gasket inserted adjacent to the open proximal end of the barrel in a fluid-tight manner while being freely slidable, a medication being contained inside the barrel, wherein the barrel has a multilayer structure in which an innermost layer and an outermost layer are both made of a polyolefin resin, and an intermediate layer is sandwiched by the innermost layer and the outermost layer and the intermediate layer is composed of at least one layer made of a resin excelling in an oxygen and/or water vapor barrier property, and further wherein:

an end of the intermediate layer in a cylindrical wall portion of the barrel is formed up to a rim of the shoulder portion;

the shoulder portion formed with the polyolefin resin has a thickness sufficient to exert an oxygen and/or water vapor barrier, property; and the luer tip is sealed by a cap having a barrier property.

* * * * *